(12) United States Patent
Ogata et al.

(10) Patent No.: US 12,730,048 B2
(45) Date of Patent: Sep. 8, 2026

(54) SUBSTANCE DETECTING SYSTEM

(71) Applicant: I-PEX Inc., Kyoto (JP)

(72) Inventors: Kenji Ogata, Ogori (JP); Shogo Kurogi, Ogori (JP)

(73) Assignee: I-PEX Inc., Kyoto (JP)

( * ) Notice: Subject to any disclaimer, the term of this patent is extended or adjusted under 35 U.S.C. 154(b) by 287 days.

(21) Appl. No.: 18/711,517

(22) PCT Filed: Oct. 31, 2022

(86) PCT No.: PCT/JP2022/040744
§ 371 (c)(1),
(2) Date: May 17, 2024

(87) PCT Pub. No.: WO2023/090140
PCT Pub. Date: May 25, 2023

(65) Prior Publication Data

US 2025/0020561 A1 Jan. 16, 2025

(30) Foreign Application Priority Data

Nov. 19, 2021 (JP) ................................ 2021-188684

(51) Int. Cl.
*G01N 5/02* (2006.01)
*G01N 33/00* (2006.01)

(52) U.S. Cl.
CPC ........... *G01N 5/02* (2013.01); *G01N 33/0031* (2013.01)

(58) Field of Classification Search
CPC ............................ G01N 5/02; G01N 33/0031
(Continued)

(56) References Cited

U.S. PATENT DOCUMENTS 4,041,768 A * 8/1977 Gibert .................. G01N 29/036 96/97
4,614,440 A * 9/1986 King .................. B01F 25/4313 366/340
(Continued)

FOREIGN PATENT DOCUMENTS

JP 2001-201436 A 7/2001
JP 2009-204584 A 9/2009
(Continued)

OTHER PUBLICATIONS

Extended European Search Report (EESR) dated Oct. 13, 2025, issued for the corresponding EP patent application No. 22895423.6, 9 pages.

*Primary Examiner* — John Fitzgerald
(74) *Attorney, Agent, or Firm* — Howard & Howard Attorneys PLLC

(57) ABSTRACT

A substance detecting system (1) includes a plurality of substrates (2). In each of the substrates (2), a plurality of through-holes (3) through which gas (G) flows is arranged. In each of the substrates (2), in at least one of the through-holes (3), a substance sensor (4) to detect a target substance contained in the gas (G) flowing through the through-hole (3) is installed. The substrates (2) are stacked in such a way that through-holes (3) corresponding to each other communicate with each other. Because of this configuration, a plurality of flow paths (5) for the gas (G) extending in the stacking direction of the substrates (2) is formed. In the substance detecting system (1), a plurality of the substance sensors (4) is arranged in at least one flow path (5).

15 Claims, 15 Drawing Sheets

(58) Field of Classification Search
USPC ........ 73/24.01, 24.03, 24.06; 366/181.5, 340
See application file for complete search history.

(56) References Cited

U.S. PATENT DOCUMENTS

| | | | | |
|---|---|---|---|---|
| 7,241,423 | B2 * | 7/2007 | Golbig | B01F 33/3017 422/138 |
| 9,395,343 | B2 * | 7/2016 | Schmid | G01N 5/02 |
| 10,589,236 | B2 * | 3/2020 | Mochizuki | B01F 27/1155 |
| 11,448,619 | B2 * | 9/2022 | Ogata | G01N 29/222 |
| 12,343,686 | B2 * | 7/2025 | Ogata | G01N 35/00871 |
| 2014/0309947 | A1 * | 10/2014 | Gryska | G01N 33/0047 702/27 |
| 2017/0016840 | A1 | 1/2017 | Bourlon et al. | |
| 2021/0278377 | A1 | 9/2021 | Ogata et al. | |
| 2021/0318209 | A1 * | 10/2021 | Nakao | G01N 29/02 |

FOREIGN PATENT DOCUMENTS

| | | | | |
|---|---|---|---|---|
| JP | 2018-173313 | A | 11/2018 | |
| JP | 2021-036243 | A | 3/2021 | |
| JP | 2021-165730 | A | 10/2021 | |
| JP | 2022-90807 | A | 6/2022 | |
| KR | 10-2018-0019432 | A | 2/2018 | |
| WO | WO-2018180589 | A1 * | 10/2018 | G01N 29/2437 |

* cited by examiner

SUBSTANCE DETECTING SYSTEM

CROSS-REFERENCE TO RELATED APPLICATIONS

This application is a U.S. National Phase Application of International Patent Application No. PCT/JP2022/040744, filed Oct. 31, 2022, which claims the benefit of JP Patent Application No. 2021-188684, filed Nov. 19, 2021, the disclosures of which are hereby incorporated by reference in their entirety.

TECHNICAL FIELD

The present disclosure relates to a substance detecting system.

BACKGROUND ART

In Patent Literature 1, a chemical sensor device serving as a substance detecting system that detects a substance, based on the amount of change in resonance frequency that occurs when the substance adsorbs to or desorbs from a sensitive film is disclosed. The chemical sensor device includes a plurality of oscillators on each of which a sensitive film exhibiting adsorption/desorption characteristics for a different substance is installed. Each of the oscillator includes a piezoelectric substrate and is vibrated by the piezoelectric substrate to which AC voltage is applied deforming. When a substance adsorbs to or desorbs from the sensitive film, resonance frequency of each oscillator changes. This configuration enables detection of a substance.

Use of the chemical sensor device enables an odor comprising a plurality of types of substances to be detected. An odor contained in the gas is identified based on a pattern of reaction values of the respective sensitive films, that is, a composition ratio of a plurality of substances causing the odor.

CITATION LIST

Patent Literature

Patent Literature 1: Unexamined Japanese Patent Application Publication No. 2009-204584.

SUMMARY OF INVENTION

Technical Problem

As described above, an odor of gas comprises a plurality of types of substances contained in the gas. Therefore, in order to accurately identify an odor of gas, a plurality of substance sensors each of which detects one of the corresponding substances is required. In this case, a region in which the plurality of substance sensors is arranged is required, and there has been an inconvenience that the larger the number of types of substances to be detected becomes, the larger the area of the region becomes.

The present disclosure has been made in consideration of the above-described circumstances, and an objective of the present disclosure is to provide a substance detecting system capable of reducing area of a region required to arrange a plurality of substance sensors.

Solution to Problem

In order to achieve the above-described objective, a substance detecting system according to a first aspect of the present disclosure includes a plurality of substrates in each of which a plurality of through-holes through which gas flows is arranged and, in at least one of the through-holes, a substance sensor to detect a target substance contained in the gas flowing through the through-hole is installed, in which by the substrates being stacked in such a manner that the through-holes communicate with each other, a plurality of flow paths for the gas, the flow paths extending in a stacking direction of the substrates, is formed, and in at least one of the flow paths, a plurality of the substance sensors is arranged.

In this case, the substance detecting system may be configured such that sizes of cross sections of the through-holes orthogonal to a direction in which the gas flows are different from each other between substrates adjacent to each other.

The substance detecting system may be configured such that size of each of the cross sections of the through-holes in a substrate on a downstream side of the flow paths is larger than size of each of the cross sections of the through-holes in a substrate on an upstream side of the flow paths.

The substance detecting system may be configured such that size of a cross section of each of the flow paths orthogonal to a direction in which the gas flows increases in a continuous manner from an upstream side toward a downstream side of the flow path.

Each of the substance sensors may include: a vibrating beam closing a portion of one of the through-holes; a sensitive film film-formed on the vibrating beam in such a manner as to face an upstream side of a flow of the gas; and a signal outputter capable of outputting a signal indicating a change in a vibration state of the vibrating beam, the change being caused by adherence of the target substance contained in the gas passing through the through-hole on the sensitive film.

The substance detecting system may be configured such that regardless of sizes of cross sections of the through-holes orthogonal to a direction in which the gas flows, size of each of the vibrating beams is defined in such a manner that resonance frequencies of the vibrating beams are uniform among the through-holes.

The substance detecting system may be configured such that the substrates are stacked in such a manner that each of the flow paths is formed by the through-hole in which the substance sensor is installed and the through-hole in which the substance sensor is not installed alternately communicating with each other.

The substance detecting system may be configured such that the substrates are stacked in such a manner that positions of at least portions of outer sides of the substrates adjacent to each other are different from each other.

The substance detecting system may be configured such that shapes, directions, or sizes of outer shapes of the substrates adjacent to each other are different from each other.

The substance detecting system may be configured such that the substrates are stacked in descending order of size of an outer shape.

The substance detecting systems may be configured such that a shape of each of cross sections orthogonal to a direction in which the gas flows in the through-holes is circular or polygonal.

The substance detecting system may be configured such that a boundary line between an edge of each of the through-holes and one of the vibrating beams is linear.

The substance detecting system may be configured such that a plurality of the substance sensors each of which detects one of different substances is arranged in the same flow path.

The substance detecting system may include a flow controller to draw in the gas from an outside and, while making flow of the gas constant, output the gas to the flow paths.

The substance detecting system may include a plurality of branch paths to divide the gas output from the flow controller into flows of gas having a same flow rate and flow velocity and send each of the flows of gas to one of the flow paths.

Advantageous Effects of Invention

According to the present disclosure, a plurality of through-holes is arranged in the substrates, and a substance sensor to detect a target substance is installed in at least one through-hole in each substrate. In the flow paths for gas formed by stacking the substrates, a plurality of substance sensors is arranged. Since because of this configuration, the number of flow paths can be reduced to a smaller number than the number of substance sensors, area of a region required to arrange a plurality of substance sensors can be reduced.

BRIEF DESCRIPTION OF DRAWINGS

FIG. 12 is a cross-sectional perspective view of the substance detecting system according to Embodiment 8 of the present disclosure;

DESCRIPTION OF EMBODIMENTS

Figure 1A:
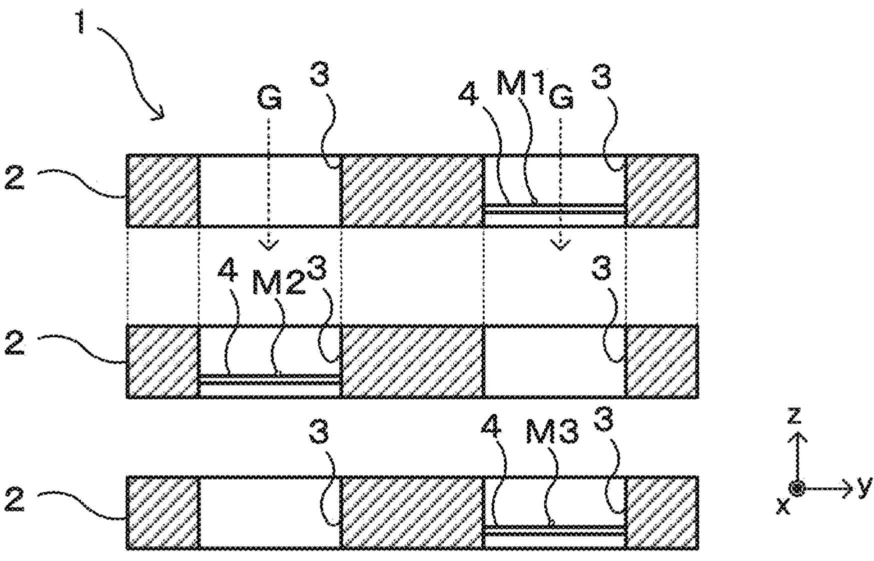
FIG. 1A is a cross-sectional view of substrates constituting a substance detecting system according to Embodiment 1 of the present disclosure.

An embodiment of the present disclosure is described below in detail with reference to the drawings. In the drawings, the same or equivalent parts are designated by the same reference numerals.

Embodiment 1

First, Embodiment 1 of the present disclosure is described. As illustrated in FIG. 1A, a substance detecting system 1 according to Embodiment 1 includes substrates 2. In FIG. 1A, three substrates 2 are illustrated. However, the substance detecting system 1 may include only two substrates 2 or may include three or more substrates 2. That is, the substance detecting system 1 includes a plurality of substrates 2.

The substrates 2 are, for example, manufactured using micro electro mechanical systems (MEMS) that is a semiconductor manufacturing technology for achieving fine processing from a silicon on an insulator (SOI) substrate. Note that the substrates 2 are not limited to SOI substrates as long as the substrates 2 are substrates in which substance sensors 4, which are described later, can be installed.

In each of the substrates 2, through-holes 3 are arranged. In FIG. 1A, two through-holes 3 are formed per substrate 2. However, three or more through-holes 3 may be formed in each substrate 2. That is, in each of the substrates 2, a plurality of through-holes 3 are formed.

Each of the through-holes 3 has a size that allows gas G to pass through the through-hole 3. In each of the substrates 2, a substance sensor 4 is installed in at least one of the through-holes 3. In FIG. 1A, two through-holes 3 are formed in each of the substrates 2, and a substance sensor 4 is installed in one of the two through-holes 3.

Each of the substance sensors 4 detects one of target substances M1, M2, and M3 that are contained in the gas G passing through the through-holes 3. That is, in the present embodiment, it is assumed that target substances to be detected are three type of substances M1 to M3. In the substance detecting system 1, three substance sensors 4 are installed. A substance sensor 4 installed in the first substrate 2 as viewed from the +z side detects the target substance M1. In addition, a substance sensor 4 installed in the second substrate 2 as viewed from the +z side detects the target substance M2. Further, a substance sensor 4 installed in the third substrate 2 as viewed from the +z side detects the target substance M3. Note that in the following description, the target substances M1 to M3 are sometimes collectively referred to as target substances M as needed.

Each of the substance sensors 4 includes a beam-shaped member that adsorbs one of the target substances M. The beam-shaped member extends from an edge of a through-hole 3 in such a manner as to close a portion of the through-hole 3. The beam-shaped member has vibration frequency changed by the target substance M adsorbing to the beam-shaped member. The substance sensor 4 detects the target substance M based on a change in the vibration frequency.

Figure 1B:
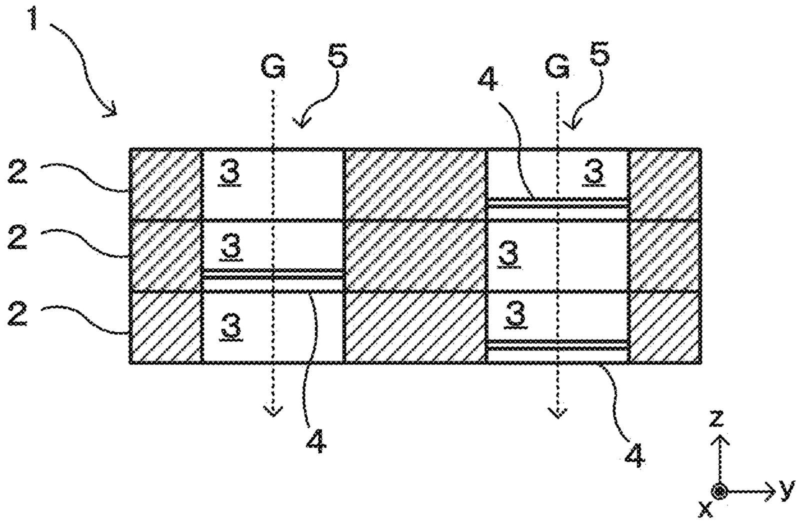
FIG. 1B is a cross-sectional view illustrating a configuration of the stacked substrates in the substance detecting system according to Embodiment 1 of the present disclosure.

Positional relationships among arrangement positions of the plurality of through-holes 3 are the same among the substrates 2. As illustrated in FIG. 1B, the substrates 2 are stacked in the thickness direction of the substrates 2 in such a way that the through-holes 3 in the substrates 2 communicate with each other. Because of this configuration, a plurality of flow paths 5 for the gas G extending in the stacking direction of the substrates 2 is formed.

In FIG. 1B, each of two through-holes 3 formed in each substrate 2 communicates with one of two through-holes 3 formed in an adjacent substrate 2, and as a result, two flow paths 5 are formed. In one of the flow paths 5, two (two stages of) substance sensors 4 are installed. That is, in the substance detecting system 1, a plurality of the substance sensors 4 is arranged in at least one flow path 5.

The gas G flows into the flow paths 5 from openings on the +z side, flows in the −z-direction in the flow paths 5, and flows out from openings on the −z side. When the target substances M are contained in the gas G, the target substances M adsorb on the substance sensors 4, and the target substances M are detected by the substance sensors 4. Note that in the following embodiments, a direction in which the gas G flows in the flow paths 5 is assumed to be the −z direction.

As described above, in the substance detecting system 1, a substance sensor 4 to detect the target substance M1, a substance sensor 4 to detect the target substance M2, and a substance sensor 4 to detect the target substance M3 are installed. The substance sensor 4 to detect the target substance M1 and the substance sensor 4 to detect the target substance M3 are installed in the same flow path 5. Thus, in the substance detecting system 1, the number of flow paths 5 to detect the three types of target substances M1 to M3 can be set to two instead of three, which is the same as the number of substance sensors 4.

As described in the foregoing, according to the substance detecting system 1 according to the present embodiment, a plurality of through-holes 3 is arranged in the substrates 2, and a substance sensor 4 to detect a target substance M is installed in at least one through-hole 3. In the flow paths 5 for the gas G formed by stacking the substrates 2, a plurality of substance sensors 4 is arranged. Since because of this configuration, the number of flow paths 5 can be reduced with respect to the number of substance sensors 4, area of a region required to arrange the plurality of substance sensors 4 can be reduced.

Note that in the present embodiment, a plurality of substance sensors 4 each of which detects one of different target substances M1 and M3 is arranged in the same flow path 5. Because of this configuration, a detection level of the target substance M3 by a substance sensor 4 on the downstream side of a flow of the gas G in the flow path 5 can be prevented from being reduced. However, the present disclosure is not limited to the configuration. It may be configured such that substance sensors 4 that detect the same type of target substance (for example, M1) are arranged in the same flow path 5. When configured in such a manner, since some particles of the target substance M1 that did not adsorb on the upstream substance sensor 4 can be caused to further adsorb on the downstream substance sensor 4, detection performance of the target substance M1 can be improved.

Embodiment 2

Next, Embodiment 2 of the present disclosure is described. An overall configuration of a substance detecting system 1 according to the present embodiment is the same as the configuration illustrated in FIG. 1A. The substance detecting system 1 according to the present embodiment is characterized by a substance sensor 4 installed in a through-hole 3 of each substrate 2.

Figure 2A:
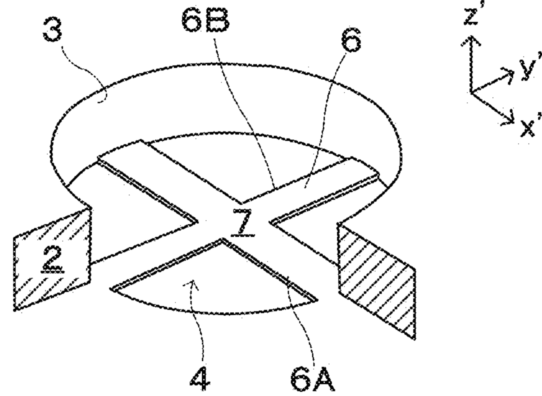
FIG. 2A is a perspective view of a substance sensor illustrated with a portion of a through-hole removed in a substance detecting system according to Embodiment 2 of the present disclosure.

As illustrated in FIG. 2A, a substance sensor 4 constituting the substance detecting system 1 according to the present embodiment includes a vibrating beam 6. The vibrating beam 6 includes a linear plate-shaped drive beam 6A and a linear plate-shaped detection beam 6B. Each of the drive beam 6A and the detection beam 6B extends from an edge portion toward an opposite edge portion of the through-hole 3 and is fixed to the edge of the through-hole 3 at both ends.

The drive beam 6A and the detection beam 6B are orthogonal to each other and are joined to each other at the center. It is assumed that a direction in which the drive beam 6A extends is an x'-direction and a direction in which the detection beam 6B extends is a y'-direction. A z'-direction coincides with the z-direction in FIGS. 1A and 1B. In the present embodiment, width of the drive beam 6A, that is, size of the drive beam 6A in the y'-direction, is larger than width of the detection beam 6B, that is, size of the detection beam 6B in the x'-direction. In addition, width of a drive electrode 8 and width of a detection electrode 9 have sizes matching the width of the drive beam 6A and the width of the detection beam 6B, respectively. However, the present disclosure is not limited to the configuration. The width of the drive beam 6A and the width of the detection beam 6B may be the same, or the width of the drive beam 6A may be smaller than the width of the detection beam 6B.

The vibrating beam 6 closes a portion of the through-hole 3 instead of the entire through-hole 3. Therefore, the vibrating beam 6 is formed in such a way that gas G does not stay in the through-hole 3 and the gas G easily passes through the through-hole 3.

On a surface on the +z' side of the vibrating beam 6, a sensitive film 7 is film-formed. Since the sensitive film 7 is film-formed in such a manner as to oppose flow of the gas G containing a target substance M, that is, in such a manner as to face the upstream side of the flow of the gas G, the sensitive film 7 is configured to be able to easily adsorb the target substance M contained in the gas. The sensitive film 7 adsorbs the target substance M. A material of which the sensitive film 7 is made is different for each type of target substance M serving as a substance to be adsorbed. Although the sensitive film 7 is only required to be film-formed on a portion of the vibrating beam 6, the sensitive film 7 may be film-formed on the entire vibrating beam 6. The larger the area of a portion where the sensitive film 7 is film-formed is increased, the more likely the sensitive film 7 adsorbs the target substance M contained in the gas G.

The target substance M is, for example, a substance contained in, for example, air among a chemical substance group constituting an odor (causes of an odor). Examples of the target substance M include odor causative substances having a characteristic odor, such as ammonia, mercaptan, an aldehyde, hydrogen sulfide, and an amine. When after the target substance M included in the odor causative substances adsorbs on the sensitive film 7, concentration of the target substance M in the gas G is reduced, and the target substance M having adsorbed desorbs from the sensitive film 7. This phenomenon enables reuse of the sensitive film 7.

The vibrating beam 6 is configured in such a manner that the target substance M adsorbing on the sensitive film 7 causes vibration frequency (for example, resonance frequency) of the vibrating beam 6 to be changed. Note that in order for vibration of the vibrating beam 6 not to be influenced by vibration of a device into which the substance detecting system 1 is incorporated, the vibration frequency of the vibrating beam 6 is preferably set in such a manner as to be different from and higher than the vibration frequency of the device.

Figure 2B:
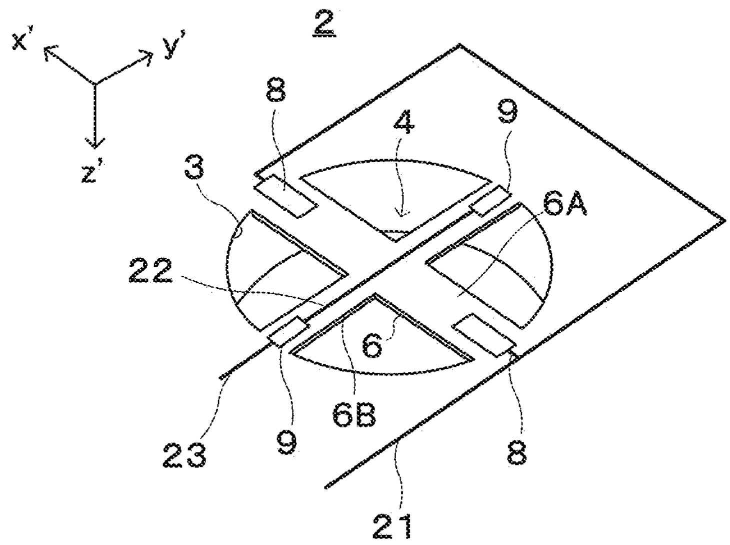
FIG. 2B is a perspective view of the substance sensor in FIG. 2A viewed from the opposite side.

On a portion of a surface on the −z' side of the vibrating beam 6, a grounded lower electrode layer is formed. Note that the lower electrode layer may be formed on the entire surface on the −z' side of the vibrating beam 6. On the lower electrode layer, a piezoelectric element layer is formed. As illustrated in FIG. 2B, on the piezoelectric element layer at both ends of the drive beam 6A, a pair of drive electrodes 8 are formed, and at both ends of the detection beam 6B, a pair of detection electrodes 9 are formed. In addition, on the substrate 2 and the vibrating beam 6, a drive signal line 21, an inter-electrode signal line 22, and a detection signal line 23 that serve as a circuit on the substrate 2 are formed. The drive signal line 21 is connected to the drive electrodes 8. In addition, the inter-electrode signal line 22 connects the detection electrodes 9 to each other on the detection beam 6B. The detection signal line 23 is connected to one of the detection electrodes 9.

A voltage signal to drive the vibrating beam 6, that is, a drive signal, is applied to the drive electrodes 8 via the drive signal line 21. By the drive signal applied to the drive electrodes 8, the vibrating beam 6 vibrates. A voltage signal from one of the detection electrodes 9 that is generated by the vibration of the vibrating beam 6, that is, a detection signal, is sent to the other of the detection electrodes 9 via the inter-electrode signal line 22. Voltage signals from the pair of detection electrodes 9 are collectively output via the detection signal line 23.

Note that it may be configured such that the drive electrodes 8 are connected to each other by the inter-electrode signal line 22 and the drive signal line 21 is connected to one of the drive electrodes 8. In this case, each of the detection electrodes 9 is connected to the detection signal line 23 and outputs a detection signal to the detection signal line 23. Note that in this case, the detection electrodes 9 may be configured such that one of the detection electrodes 9 is connected to the detection signal line 23 and the other of the detection electrodes 9 serves as a dummy electrode and is not connected to the detection signal line 23.

As described above, the substance sensor 4 includes the vibrating beam 6 closing a portion of the through-hole 3, the sensitive film 7 film-formed on the vibrating beam 6 in such a manner as to face the upstream side of the flow of the gas G, and a signal outputter (detection electrodes 9) capable of outputting a signal indicating a change in a vibration state of the vibrating beam 6 caused by adsorption, on the sensitive film 7, of the target substance M contained in the gas G passing through the through-hole 3.

Note that the width of the drive beam 6A is larger than the width of the detection beam 6B. In addition, the width of the drive electrodes 8 is larger than the width of the detection electrodes 9. Because of this configuration, by not only strengthening a force vibrating the vibrating beam 6 but also increasing vibration displacement of the detection beam 6B, detection precision can be improved. In addition, each of the drive electrodes 8 and the detection electrodes 9 may be formed over the vibrating beam 6 and an edge portion of the through-hole 3. Since stress generated by vibration of the vibrating beam 6 is maximized at a boundary between the edge portion of the through-hole 3 and the vibrating beam 6, a drive force of the vibrating beam 6 and a detection level of a detection signal can be increased.

Figure 3:
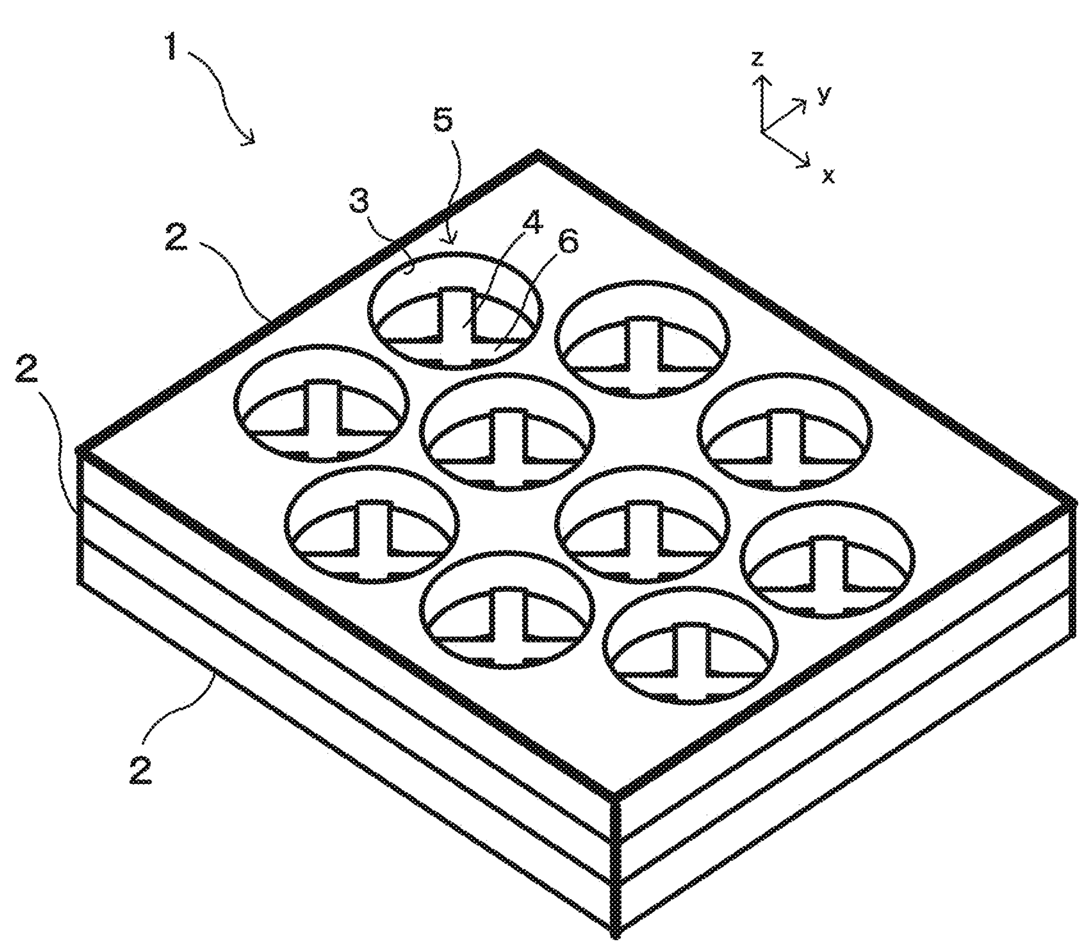
FIG. 3 is a perspective view illustrating a configuration of stacked substrates in the substance detecting system according to Embodiment 2 of the present disclosure.

As illustrated in FIG. 3, in the substance detecting system 1 according to the present embodiment, not only are ten through-holes 3 formed in each of the substrates 2 but also a substance sensor 4 is installed in each of the through-holes 3. Because of this configuration, the number of substance sensors 4 can be set to 30. When it is configured such that a substance sensor 4 is installed in each through-hole 3 formed in all the substrates 2 as described above, the number of types of target substances M to be detected can be increased to the maximum extent possible.

In addition, in the substance detecting system 1, no substrate in which some substance sensors 4 are not formed is interposed between substrates 2. Thus, the substance sensors 4 can be arranged close to each other. Because of this configuration, not only can detection sensitivity be improved but also variation in detection levels can be suppressed, and in addition thereto, the entire device can be miniaturized.

In addition, in the present embodiment, the vibrating beam 6 is formed in a structure in which two doubly supported beams, namely the drive beam 6A and the detection beam 6B, are joined at the center. When configured in such a manner, by causing one drive beam 6A to vibrate the entire vibrating beam 6 and the other detection beam 6B to detect vibration of the vibrating beam 6, wiring saving can be achieved with respect to wiring of a circuit to drive the vibrating beam 6 and wiring of a circuit to detect vibration of the vibrating beam 6.

In addition, in the present embodiment, the drive beam 6A and the detection beam 6B are orthogonal to each other. When configured in such a manner, the detection beam 6B can be configured not to prevent vibration of the drive beam 6A. However, the drive beam 6A and the detection beam 6B do not have to be orthogonal to each other and are only required to cross each other.

In addition, in the above-described embodiment, the drive electrodes 8 are formed at both ends of the drive beam 6A, and the detection electrodes 9 are formed at both ends of the detection beam 6B. However, the present disclosure is not limited to the configuration. In the substance detecting system 1, a drive electrode 8 may be formed at one end of the drive beam 6A, and a detection electrode 9 may be formed at one end of the detection beam 6B. In other words, in the substance detecting system 1, no drive electrode 8 has to be formed at the other end of the drive beam 6A, and no detection electrode 9 has to be formed at the other end of the detection beam 6B.

Figure 4A:
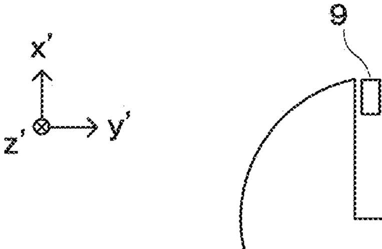
FIG. 4A is a diagram illustrating a case where a vibrating beam is a cantilever.

In addition, in the present embodiment, the vibrating beam 6 constituting the substance sensor 4 is configured to be a cross-shaped beam that has four ends fixed to the edge of the through-hole 3. However, the present disclosure is not limited to the configuration. As illustrated in FIG. 4A, the vibrating beam 6 may be a cantilever. In this case, the vibration frequency of the vibrating beam 6 is preferably increased by increasing width or thickness of the vibrating beam 6. In this case, the drive electrode 8 and the detection electrode 9 are only required to be formed together at an end (an end fixed to the edge of the through-hole 3) of the vibrating beam 6. In addition, it may be configured such that, of the drive electrode 8 and the detection electrode 9, one electrode is formed at an end of the vibrating beam 6 and the other electrode is formed at the other end of the vibrating beam 6. A free end of the vibrating beam 6 may extend to a vicinity of the edge of the through-hole 3.

Figure 4B:
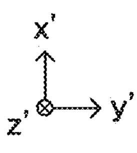
FIG. 4B is a diagram illustrating a case where the vibrating beam is a doubly supported beam.
Figure 4B:
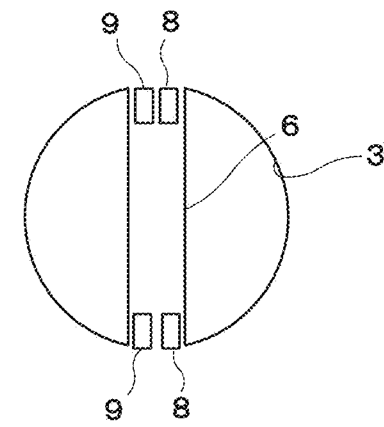

In addition, as illustrated in FIG. 4B, a vibrating beam 6 that is fixed to the edge of the through-hole 3 at two points may be used. In this case, it is only required that pairs of a drive electrode 8 and a detection electrode 9 are formed at both ends of the vibrating beam 6. In addition, it may be configured such that a drive electrode 8 is formed at one end of the vibrating beam 6 and a detection electrode 9 is formed at the other end of the vibrating beam 6. In addition, it may be configured such that, of a drive electrode 8 and a detection electrode 9, one electrode is formed at an end of the vibrating beam 6 and the other electrode is formed at the center of the vibrating beam 6.

Figure 4C:
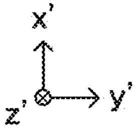
FIG. 4C is a diagram illustrating a case where the vibrating beam is fixed to an edge of a through-hole at three points.
Figure 4C:
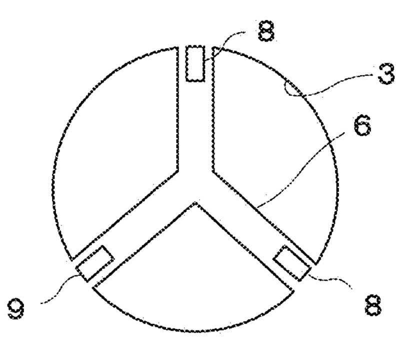

In addition, as illustrated in FIG. 4C, a vibrating beam 6 that is fixed to the edge of the through-hole 3 at three points may be used. In this case, it may be configured such that a pair of drive electrodes 8 are arranged at two ends among the ends of the vibrating beam 6 and a detection electrode 9 is arranged at the remaining end. In addition, positions of the drive electrodes 8 and a position of the detection electrode 9 may be changed. In addition, it may be configured such that, of a drive electrode 8 and a detection electrode 9, one electrode is formed at an end of the vibrating beam 6 and the other electrode is formed at the center of the vibrating beam 6.

In addition, in the present embodiment, the sensitive film 7 is formed on the surface on the +z' side of the vibrating beam 6, and the drive electrodes 8 and the detection electrodes 9 are formed on the surface on the −z' side of the vibrating beam 6. However, the present disclosure is not limited to the configuration. The sensitive film 7 may be film-formed on the surface on the −z' side in conjunction with the drive electrodes 8 and the detection electrodes 9. In this case, the sensitive film 7 is only required to be formed at a portion where neither the drive electrodes 8 nor the detection electrodes 9 are formed. In addition, it may be configured such that an insulating layer is formed on the drive electrodes 8 and the detection electrodes 9 and the sensitive film 7 is formed on the insulating layer.

Embodiment 3

Figure 5A:
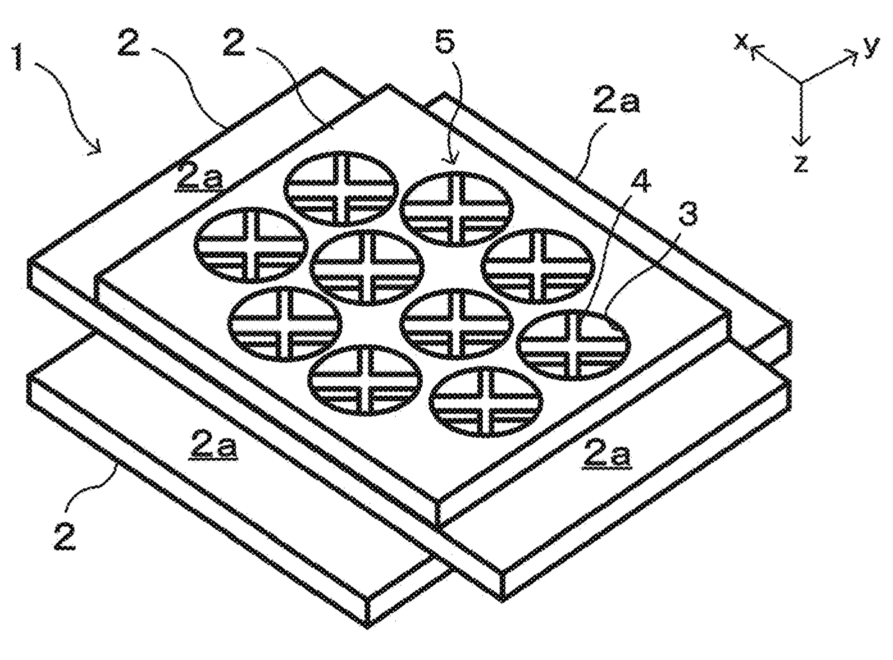
FIG. 5A is a perspective view of stacked substrates in a substance detecting system according to Embodiment 3 of the present disclosure.
Figure 5B:
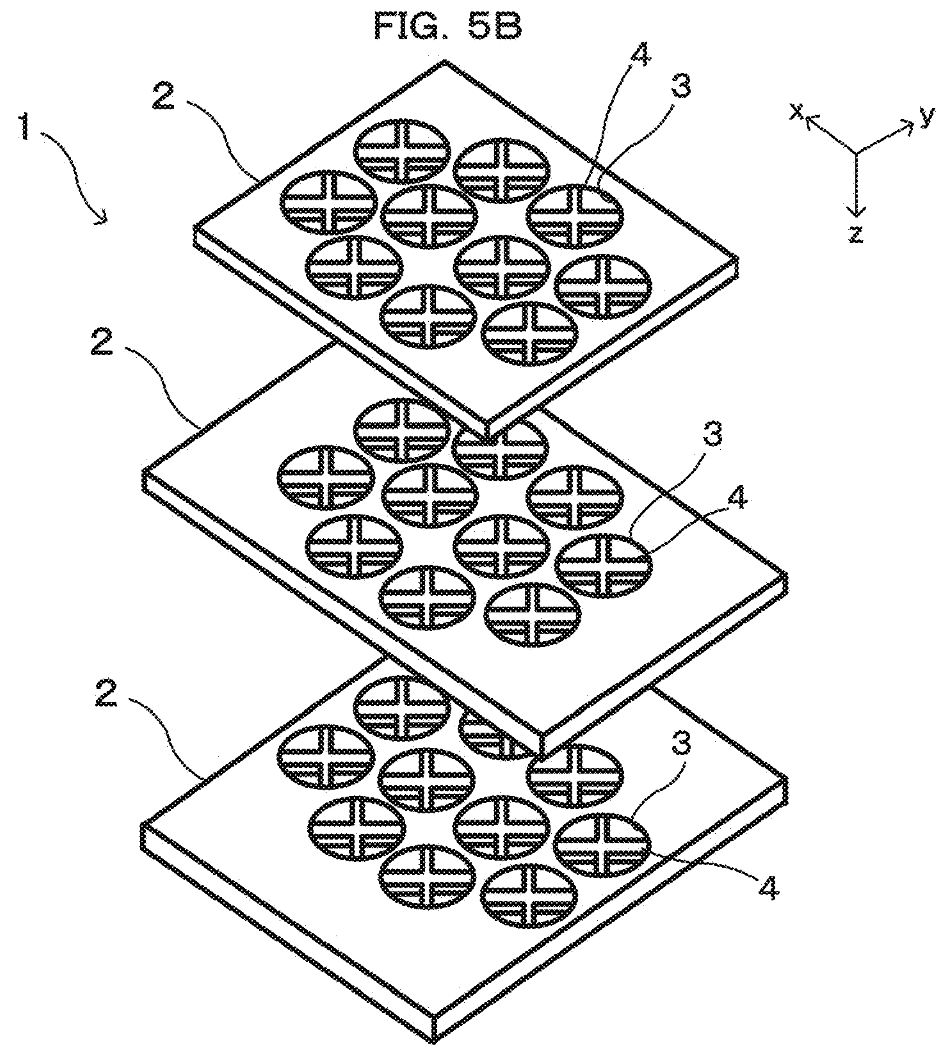
FIG. 5B is a perspective view of the substrates constituting the substance detecting system in FIG. 5A.

Next, Embodiment 3 of the present disclosure is described. As illustrated in FIGS. 5A and 5B, a substance detecting system 1 according to the present embodiment is the same as the substance detecting system 1 according to Embodiment 2 described above in having a configuration in which three substrates 2 are stacked.

As illustrated in FIG. 5A, in the substance detecting system 1 according to the present embodiment, the substrates 2 are stacked in such a manner that positions of at least portions of outer sides of substrates 2 adjacent to each other are different from each other.

More specifically, as illustrated in FIG. 5B, shapes, directions, and sizes of outer shapes of substrates 2 adjacent to each other among the substrates 2 to be stacked are different from each other. Specifically, an outer shape of the middle substrate 2 has a shape projecting to both sides in the x-axis direction with respect to an outer shape of the substrate 2 on the most −z side. The substrates 2 have different shapes and sizes from one another. Due to differences in the shape and size, exposed portions 2*a* that are exposed to the outside are formed on both sides in the x-axis direction of the middle substrate 2.

In addition, the longitudinal direction of the substrate 2 on the most +z side is aligned with the y-axis direction and is different from the longitudinal direction of the middle substrate 2. The substrates 2 have different directions from each other. Due to a difference in the direction, exposed portions 2*a* that are exposed to the outside are formed on both sides in the y-axis direction of the substrate 2 on the most +z side.

It may be configured such that on the exposed portions 2*a* on each substrate 2, an electrode to connect a drive signal line 21 and a signal source to each other is formed and an electrode to connect a detection signal line 23 and a not-illustrated detection device to each other is formed. In addition, on the exposed portions 2*a*, fixing portions to fix the substrate 2 to a housing may be formed.

Figure 6:
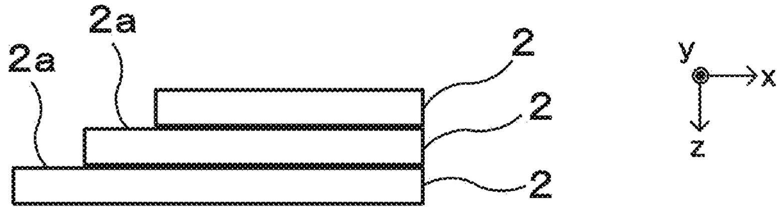
FIG. 6 is a diagram illustrating another example of substrates to be stacked.

In this case, as illustrated in FIG. 6, the substrates 2 may be configured to be stacked in descending order of the size of the outer shape. When configured in such a manner, an exposed portion 2*a* that is exposed to the −z side can be formed on each substrate 2, as a result of which electrodes can be formed on the same −z side. In addition, as illustrated in FIG. 6, it becomes possible to form the exposed portions 2*a* only on one side in the x-axis direction, that is, the −x side, and align positions at which the electrodes are formed with respect to all the substrates 2.

Embodiment 4

Figure 7A:
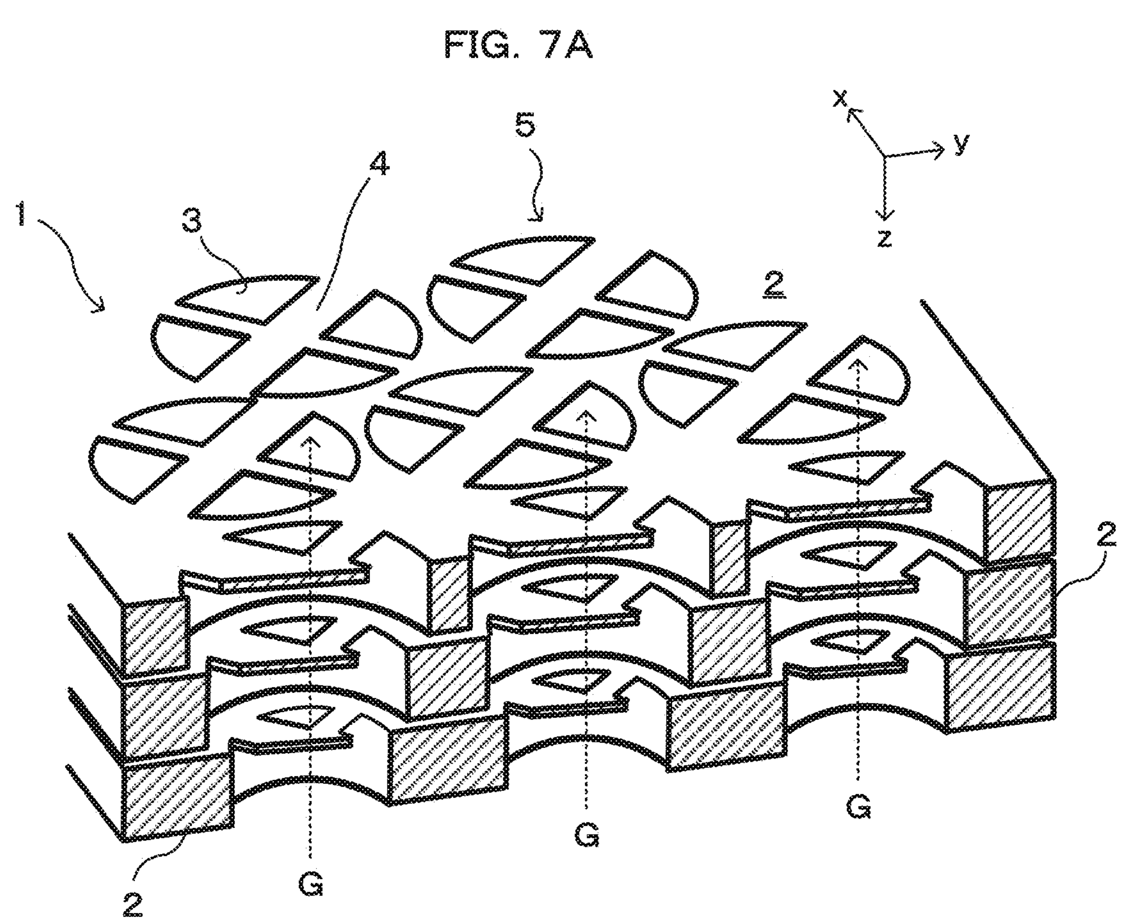
FIG. 7A is a perspective view of stacked substrates in a substance detecting system according to Embodiment 4 of the present disclosure.

Next, Embodiment 4 of the present disclosure is described. As illustrated in FIG. 7A, a substance detecting system 1 according to the present embodiment has a configuration in which three substrates 2 are stacked. In FIG. 7A, gas G flows in flow paths 5 from the lower side to the upper side of the plane of paper.

In the substance detecting system 1 according to the present embodiment, sizes of cross sections orthogonal to a direction in which the gas G flows in through-holes 3 are different from each other between substrates 2 adjacent to each other. More specifically, size of a cross section of a through-hole 3 in a substrate 2 on the downstream side of a flow path 5 is configured to be larger than size of a cross section of a through-hole 3 in a substrate 2 on the upstream side of the flow path 5.

Increasing the sizes of cross sections from the upstream side toward the downstream side of a flow path 5 causes speed of flow of the gas G on the downstream side to be slowed and a substance sensor 4 to easily adsorb a target substance M and thereby enables detection precision to be improved.

In the substrates 2 to be stacked, as the cross sections of the through-holes 3 increase, widths of vibrating beams 6 increase. Specifically, regardless of the cross sections of the through-holes 3, the widths of the vibrating beams 6 are defined in such a manner that resonance frequencies of the vibrating beams 6 are uniform.

Note that in order to make the resonance frequencies of the vibrating beams 6 uniform, thicknesses (sizes in the thickness direction of the substrates 2) of the vibrating beams 6 may be configured to be defined.

When the sizes of the through-holes 3 change as described above, lengths of the vibrating beams 6 increase, and the resonance frequencies of the vibrating beams 6 decrease. Thus, the lengths, widths, and thicknesses of the vibrating beams 6 can be determined in such a manner that resonance frequencies of the vibrating beams 6 are uniform. That is, the sizes of the vibrating beams 6 are defined in such a manner that regardless of the sizes of the cross sections of the through-holes 3, the resonance frequencies of the vibrating beams 6 are the same among the through-holes 3.

Figure 7B:
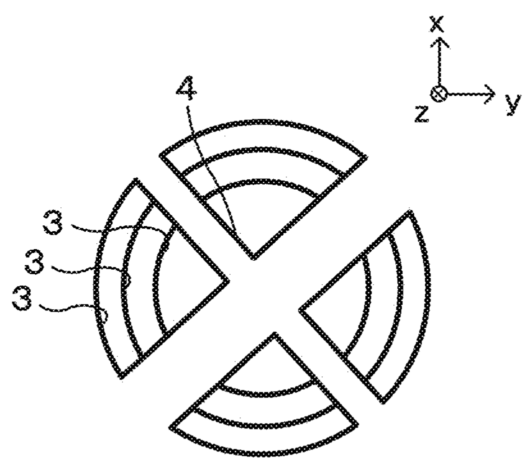
FIG. 7B is a diagram of a through-hole viewed from the −z side in the substance detecting system in FIG. 7A.

When the substance detecting system 1 is manufactured, a process of stacking the substrates 2 is performed. In the process, since as illustrated in FIG. 7B, edges of the through-holes 3 of all the substrates 2 can be seen from the −z side, it is possible to align positions of the substrates 2 while confirming that the through-holes 3 of three substrates 2 concentrically overlap one another. Because of this configuration, the substrates 2 can be stacked with the positions of the substrates 2 accurately aligned.

Embodiment 5

Figure 8:
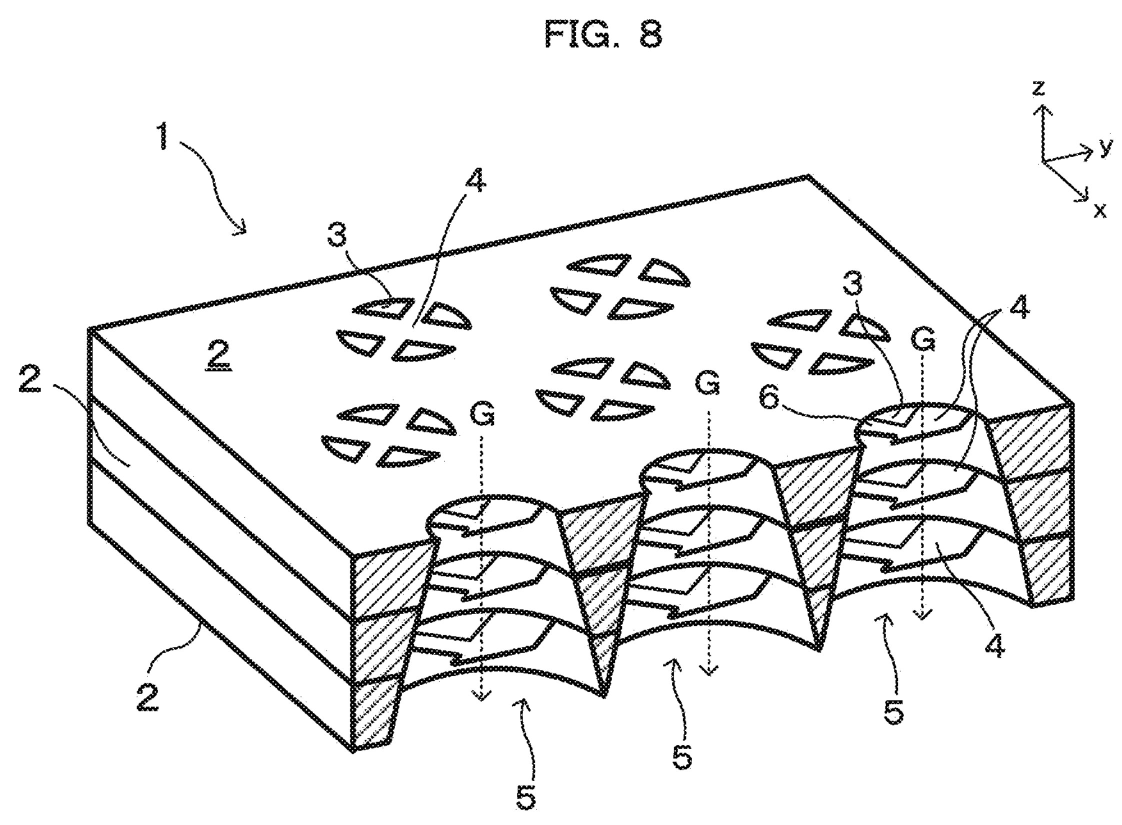
FIG. 8 is a perspective view of substrates constituting a substance detecting system according to Embodiment 5 of the present disclosure.

Next, Embodiment 5 of the present disclosure is described. As illustrated in FIG. 8, a substance detecting system 1 according to the present embodiment has a configuration in which three substrates 2 are stacked.

In the present embodiment, gas G flows in flow paths 5 from the upper side to the lower side of the plane of paper. In the present embodiment, on a surface on the +z side of a vibrating beam 6 of each substance sensor 4, a sensitive film 7 is formed.

In the substance detecting system 1 according to the present embodiment, sizes of cross sections orthogonal to a direction in which the gas G flows in through-holes 3 are different from each other between substrates 2 adjacent to each other. More specifically, size of a cross section of a through-hole 3 in a substrate 2 on the downstream side of a flow path 5 is larger than size of a cross section of a through-hole 3 in a substrate 2 on the upstream side of the flow path 5.

Further, in the present embodiment, size of a cross section of a flow path 5 that is orthogonal to the direction in which the gas G flows increases in a continuous manner from the upstream side toward the downstream side of the flow path 5. That is, inner side surfaces of through-holes 3 in communication with each other are continuously joined to each other in such a manner that an unevenness is not generated at a joint between the inner side surfaces. When configured in such a manner, in a flow path 5, objects serving as obstacles for a flow of the gas G can be eliminated as much as possible and the flow can be made uniform.

Note that in the substance detecting system 1, if the amount of adhesion of a target substance M onto the sensitive films 7 increases and detection precision is accordingly improved, the size of the cross section of a flow path 5 formed by through-holes 3 may be configured to be gradually reduced from the upstream side toward the downstream side of the flow of the gas G. A shape of each flow path 5 can be defined in such a manner that detection sensitivity increases according to characteristics of a target substance M to be detected.

Embodiment 6

Figure 9A:
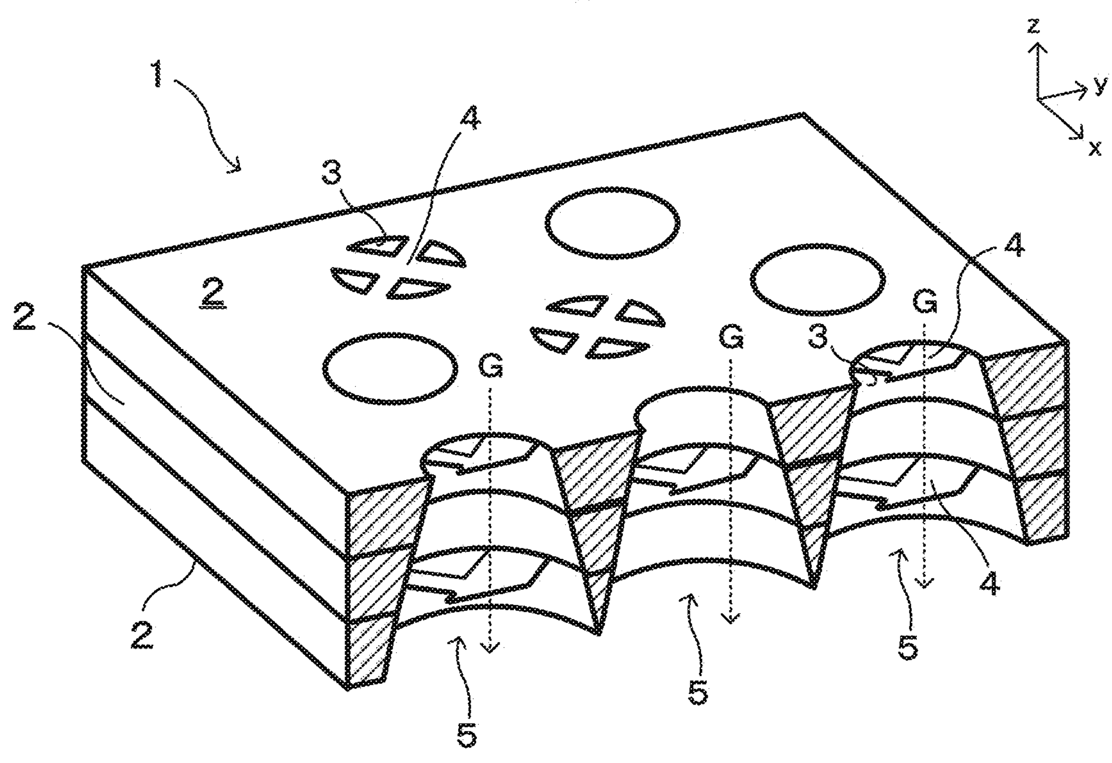
FIG. 9A is a perspective view of stacked substrates in a substance detecting system according to Embodiment 6 of the present disclosure.
Figure 9B:
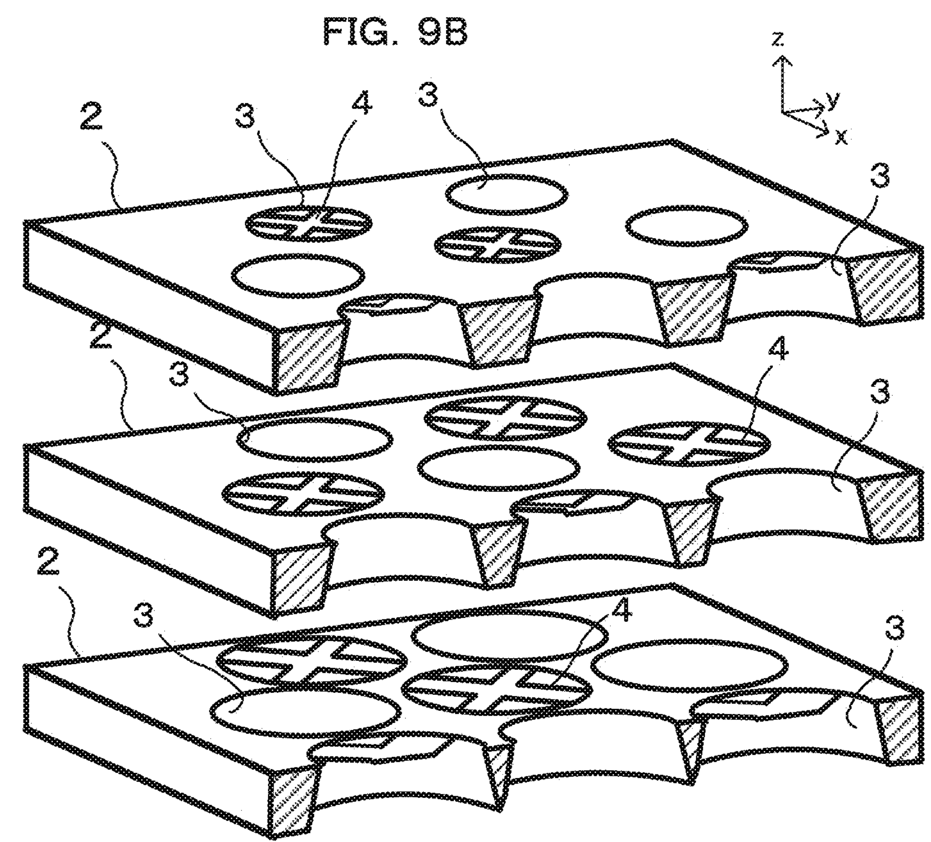
FIG. 9B is a perspective view of the substrates constituting the substance detecting system in FIG. 9A.

Next, Embodiment 6 of the present disclosure is described. In the substance detecting system 1 illustrated in FIG. 8, a substance sensor 4 is installed in each through-hole 3. In contrast, as illustrated in FIGS. 9A and 9B, in a substance detecting system 1 according to the present embodiment, substrates 2 are stacked in such a manner that a flow path 5 is formed by a through-hole 3 in which a substance sensor 4 is installed and a through-hole 3 in which no substance sensor 4 is installed alternately communicating with each other.

By interposing a through-hole 3 in which no substance sensor 4 is installed, concentration of a target substance M being reduced caused by arranging substance sensors 4 too densely and detection sensitivity being thereby reduced can be prevented. This is because it is considered that excessively dense arrangement of substance sensors 4, for example, causes flow of gas G to be changed due to a vibrating beam 6 on the upstream side and the gas G to be unlikely to come into contact with a sensitive film 7 on a vibrating beam 6 on the downstream side.

Note that in the present embodiment, the substance sensors 4 are configured to be alternately installed in the through-holes 3 forming a flow path 5. However, the present disclosure is not limited to the configuration. It is only required that no substance sensor 4 is installed in at least one through-hole 3.

Embodiment 7

Figure 10A:
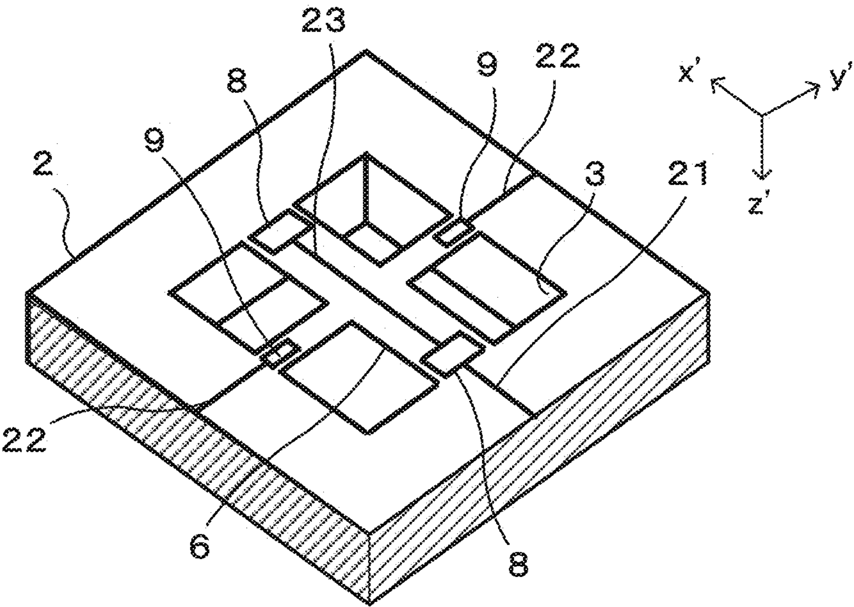
FIG. 10A is a perspective view of a through-hole formed in a substrate in a substance detecting system according to Embodiment 7 of the present disclosure.

Next, Embodiment 7 of the present disclosure is described. In the substance detecting systems 1 according to the above-described embodiments, a shape of a cross section orthogonal to the direction in which the gas G flows in a through-hole 3 is circular. In contrast, as illustrated in FIG. 10A, in a substance detecting systems 1 according to the present embodiment, a shape of a cross section orthogonal to a direction in which gas G flows in a through-hole 3 is quadrilateral.

Figure 10B:
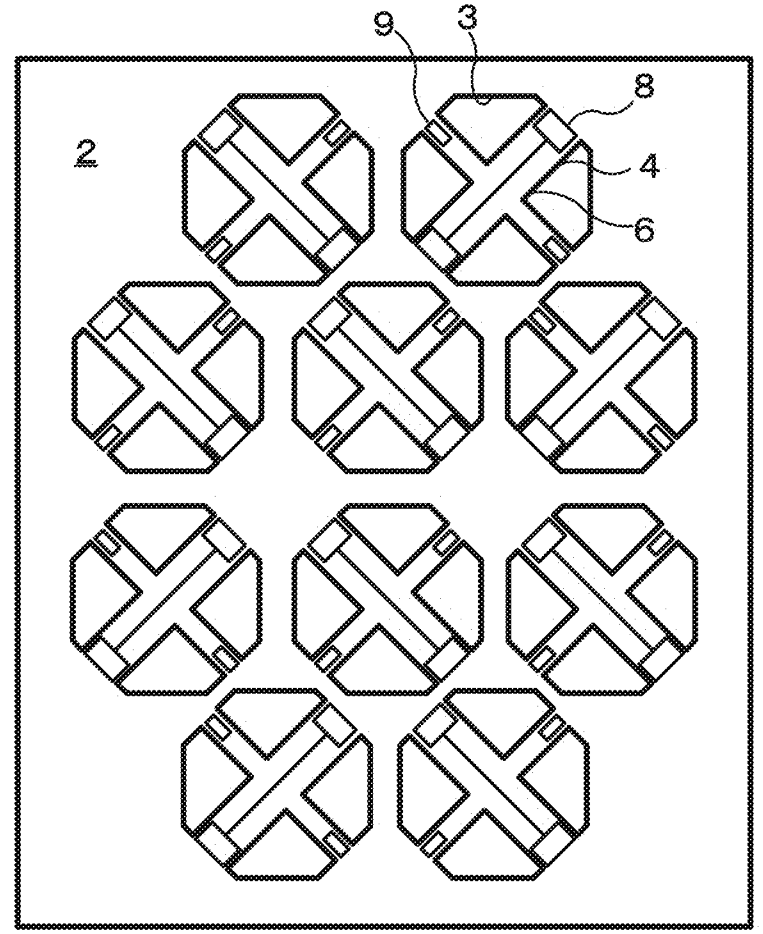
FIG. 10B is a top view of a substrate in which through-holes serving as a variation of the through-hole in FIG. 10A are formed.
Figure 10B:
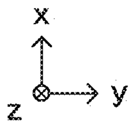

Alternatively, as illustrated in FIG. 10B, in the substance detecting system 1 according to the above-described embodiment, shapes of cross sections orthogonal to the direction in which the gas G flows in the through-holes 3 are octagonal. As described above, a cross-sectional shape of each through-hole 3 can be set to a polygon. Setting the shapes of the cross sections of the through-holes 3 to be polygonal enables the through-holes 3 in the substrates 2 to be arranged closer to each other than setting the shapes of the cross sections of the through-holes 3 to be circular.

In addition, in the present embodiment, a boundary line between a vibrating beam 6 and an edge portion of a through-hole 3 is linear. When the boundary line is formed in a straight line, local stress concentration can be prevented from occurring around the boundary line and a vibration state of the vibrating beam 6 can be brought into a state with low distortion.

In addition, when the shapes of cross sections orthogonal to the direction in which the gas G flows in the through-holes 3 are changed from a circle to a polygon inscribed in the circle, the sizes of the cross sections of the through-holes 3 can be reduced. Because of this configuration, the gas G becomes likely to come into contact with the sensitive films 7 on the vibrating beams 6. In addition, mechanical strength of the substrates 2 can be improved.

Embodiment 8

Figure 11:
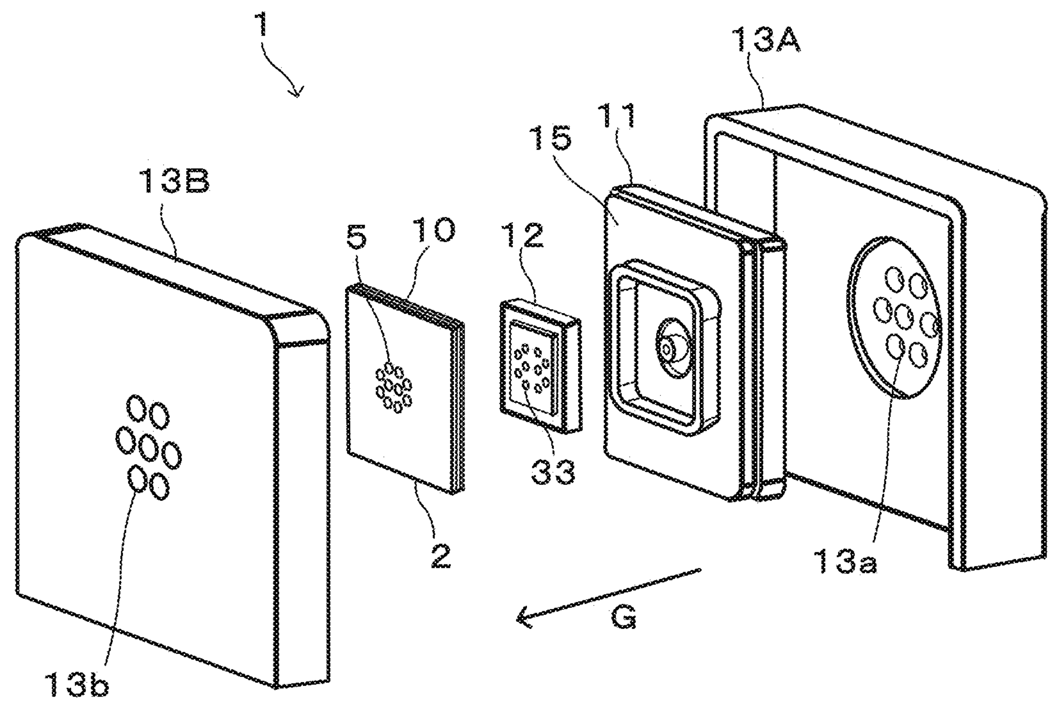
FIG. 11 is an exploded perspective view of a substance detecting system according to Embodiment 8 of the present disclosure.
Figure 12:
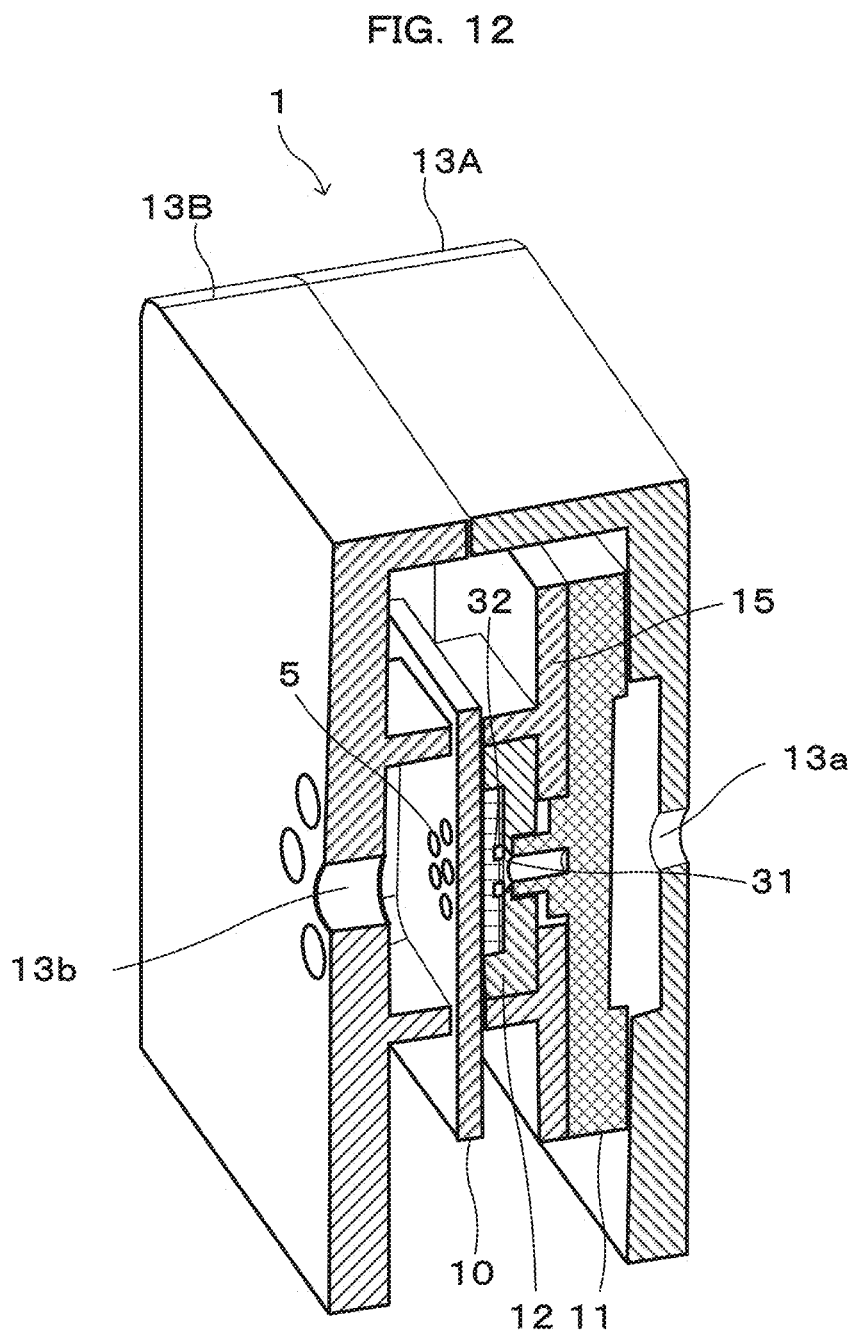

Next, Embodiment 8 of the present disclosure is described. As illustrated in FIGS. 11 and 12, a substance detecting system 1 according to the present embodiment includes a sensor 10. The sensor 10 is a sensor including a plurality of flow paths 5 that are formed by substrates 2 being stacked in Embodiments 1 to 7 described above.

The substance detecting system 1 further includes a flow controller 11, a rectifier 12 including a plurality of branch paths, and housings 13A and 13B.

The flow controller 11 is arranged at a most upstream point in a flow of gas G. The flow controller 11 is a pump or a blower that draws in and blows out the gas G. In the present embodiment, the flow controller 11 is arranged on the upstream side of the rectifier 12 in the flow of the gas G. The flow controller 11 causes the gas G to flow into the rectifier 12. In the present embodiment, the flow controller 11 blows out the inflowing gas G to the rectifier 12.

The flow controller 11 is capable of controlling start and end of drive. Driving time by the flow controller 11 can be set to a fixed period at the time of detection.

The rectifier 12 is disposed between the flow controller 11 and the sensor 10 in the flow of the gas G. The rectifier 12 lets the gas G blowing out from the flow controller 11 flow in. The rectifier 12 uniformly controls flow of the gas that has flowed in and sends the controlled gas flow to respective ones of the plurality of flow paths 5 of the sensor 10. As used herein, "uniformly controlling" means controlling the flow of the gas G in such a way that flows of the gas G are considered to be uniform with or equal to one another among the flow paths 5. The rectifier 12 rectifies the flow of the gas G in such a way that flow rates and flow velocities of flows of the gas G that are sent to respective ones of the plurality of flow paths 5 are made uniform.

Figure 13:
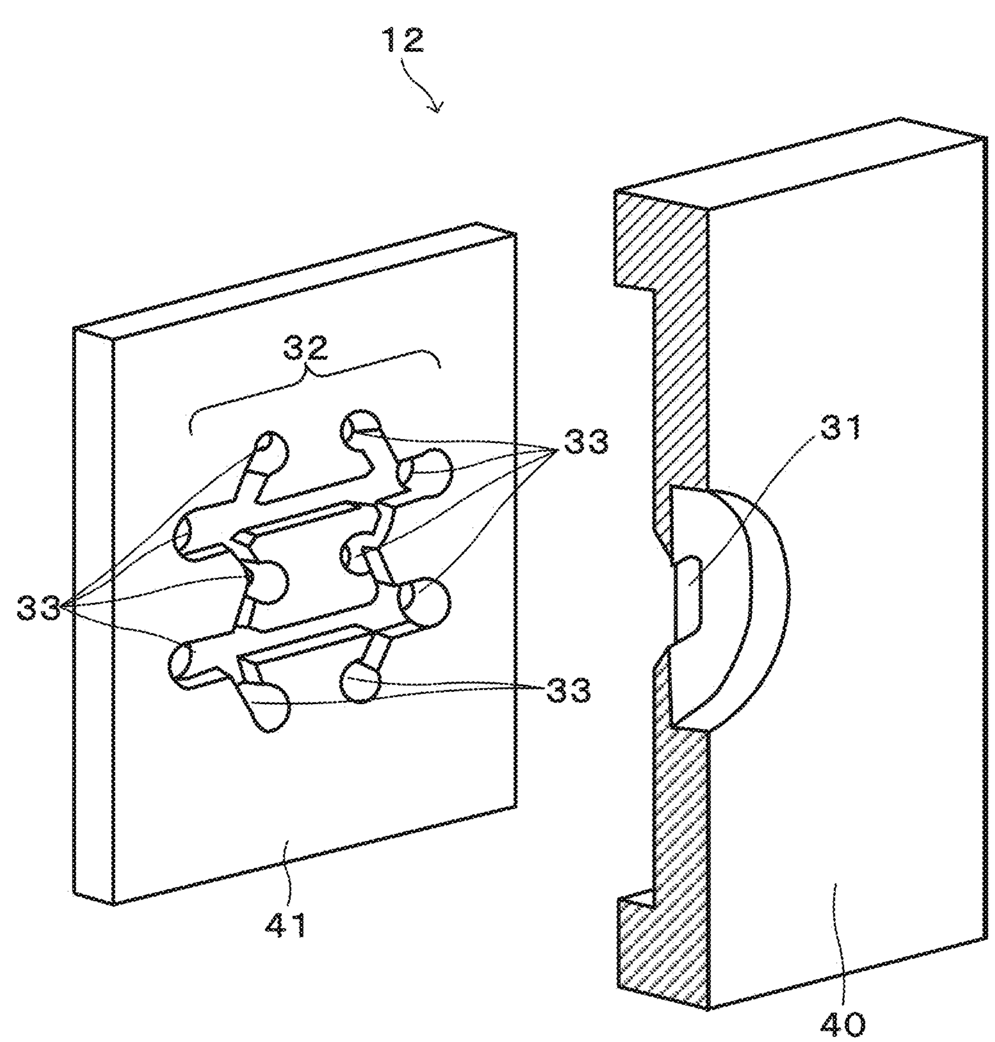
FIG. 13 is a cross-sectional perspective view illustrating a rectifier by removing a portion of the rectifier and exploding the rectifier.
Figure 14:
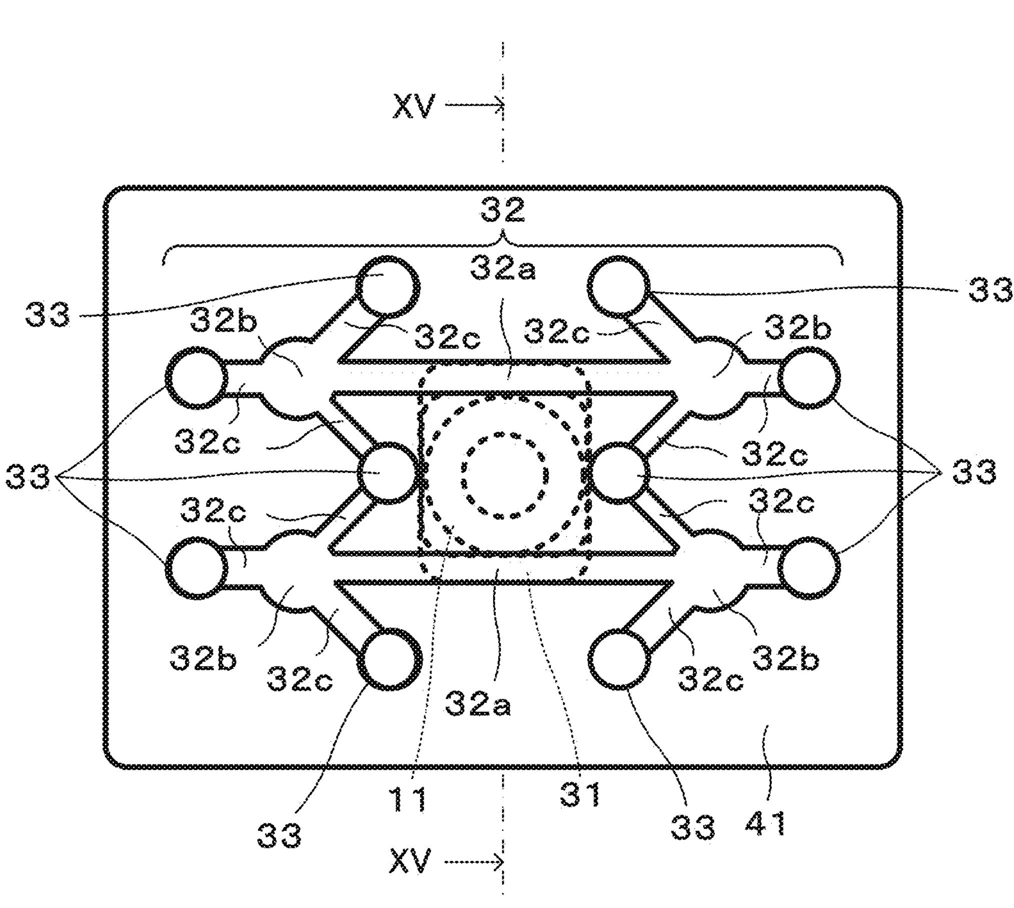
FIG. 14 is a top view of a second rectification substrate.
Figure 15:
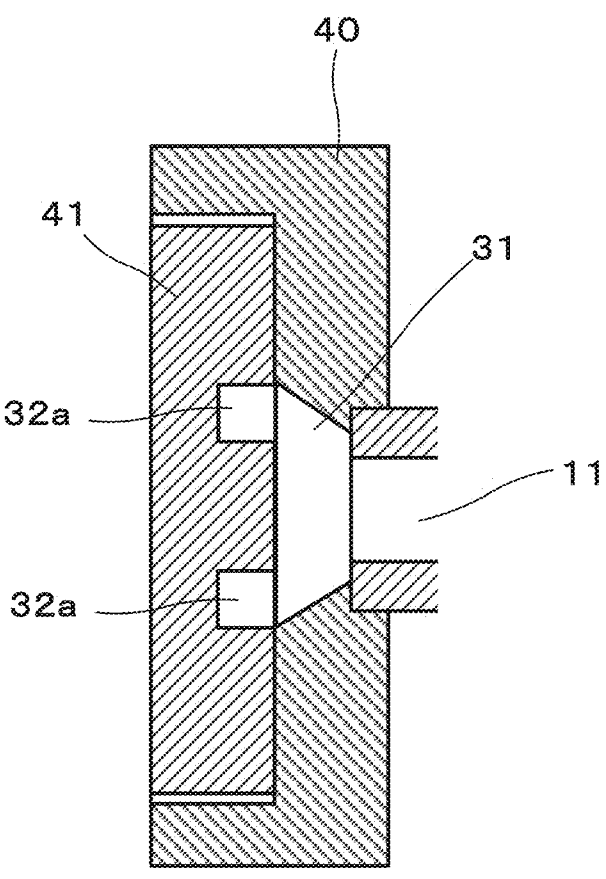
FIG. 15 is a cross-sectional view taken along the line XV-XV in FIG. 14.

As illustrated in FIGS. 13, 14, and 15, the rectifier 12 includes a first rectification substrate 40 and a second rectification substrate 41. In the first rectification substrate 40, an inflow hole 31 is formed. In the second rectification substrate 41, branch paths 32 and outflow holes 33 are formed.

As illustrated in FIG. 13, the inflow hole 31 located on the most upstream side penetrates through the first rectification substrate 40. One end, that is, an upstream end, of the inflow hole 31 is arranged in accordance with a position of a blow-out port of the flow controller 11. As illustrated in FIG. 15, the inflow hole 31 lets the gas G blown out from the flow controller 11 flow in.

As illustrated in FIGS. 14 and 15, in the branch paths 32, two flow paths 32*a*, both end portions 32*b*, and flow paths 32*c* are formed. The two flow paths 32*a* extend in parallel with each other. Central portions of respective ones of the flow paths 32*a* are in communication with the inflow hole 31. The gas G blown out from the flow controller 11 flows into the flow paths 32*a* from the inflow hole 31. The gas G, after flowing toward the both end portions 32*b* of each flow path 32*a*, flows into flow paths 32*c* branching off from the both end portions 32*b* and reaches ends of the flow paths 32*c*. The ends of the flow paths 32*c* are in communication with outflow holes 33, and the gas G is sent to the flow paths 5 of the sensor 10 via the outflow holes 33.

Shapes of the branch paths 32 are defined in such a way that flow rates and flow velocities of flows of the gas G that are supplied to respective ones of the plurality of outflow holes 33 are the same. Note that some of the outflow holes 33 are formed at merging points of two flow paths 32*c*. Width of two flow paths 32*c* that are formed extending toward a merging point is half the width of the other flow paths 32*c*. This configuration makes uniform the flow rates of flows of the gas G flowing to all the outflow holes 33.

An outflow hole 33 is disposed with respect to each flow path 5. The outflow holes 33 communicate the branch paths 32 with the flow paths 5. Each of the plurality of outflow holes 33 has the same shape and size.

Operation of the above-described substance detecting system 1 is the same as the operation of the substance detecting system 1 according to Embodiment 1 described above. First, the flow controller 11 is powered on, and blowing-in of the gas G is started. The gas G having flowed in from an inlet 13*a* of the housing 13A is drawn into the flow controller 11, and the flow controller 11 causes the gas G having flowed in to flow into the inflow hole 31 of the rectifier 12. The gas G supplied to the inflow hole 31 flows into the branch paths 32.

In the flow paths 32*a* in the branch paths 32, directions of flows of the gas G are changed, and the gas G advances to the both end portions 32*b*. The gas G having advanced to the both end portions 32*b* further advances in the flow paths 32*c* and reaches the outflow holes 33. That is, the gas G branches off into flows of the gas G by the flow paths 32*a* with flow velocity controlled, and the branched-off flows of the gas G flow into the respective outflow holes 33 in such a manner that the flow rates and flow velocities of the flows are the same among the outflow holes 33.

The gas G having flowed into the respective outflow holes 33 is supplied to the flow paths 5 of the sensor 10 at the same flow velocity and the same flow rate. The gas G supplied to the flow paths 5, after coming into contact with the sensitive films 7, is discharged from the flow paths 5.

Since as described above, the substance detecting system 1 according to the present embodiment is capable of causing the gas G to come into contact with each sensitive film 7 at a uniform flow rate and flow velocity, it becomes possible to accurately measure a ratio of reaction values at the respective sensitive films 7.

The housings 13A and 13B are a housing of the substance detecting system 1. In the housing 13A, the inlet 13*a* for the gas G is formed. In the inlet 13*a*, a replaceable filter is attached. The filter prevents intrusion of foreign objects caused by inflow of the gas G. In addition, in the housing 13B, an outlet 13*b* for the gas G is formed. Note that the substance detecting system 1 according to the present embodiment includes an internal frame 15. The internal frame 15 and the housing 13B internally sandwich the rectifier 12 and the sensor 10.

In addition, in the present embodiment, it becomes possible to detect a plurality of types of target substances M contained in the gas G. When configured in such a manner, it also becomes possible to detect a plurality of odors contained in the gas G. Since the flow rates and flow velocities of flows of the gas G flowing around the respective sensitive films 7 are uniform, it becomes possible to accurately calculate a ratio of odors contained in the gas G, based on detected substances.

In addition, as in the present embodiment, not only a portion to disperse flow of the gas G but also a portion to merge flows of the gas G can be formed in the rectifier 12. In any case, it is only required that the flows of the gas G flowing into the flow paths 5 of the sensor 10 are made uniform. The flow paths in the rectifier 12 can be determined based on a result of fluid simulation of the gas G.

As described in the foregoing, in order to draw in the gas G from the outside and, while making the flow of the gas G constant, output the gas G to the flow paths 5, the flow controller 11 sends the gas to the rectifier 12. The plurality of branch paths 32 in the rectifier 12 divides the gas G output from the flow controller 11 into flows of the gas G having the same flow rate and flow velocity and sends each of the flows of the gas G to one of the flow paths 5.

In the present embodiment, the flow controller 11 is configured to be disposed on the upstream side of the rectifier 12 and the sensor 10. However, the present disclosure is not limited to the configuration. The flow controller 11 may be disposed on the downstream side of the rectifier 12 and the sensor 10 or may be disposed on both the upstream side and the downstream side.

In addition, in the substance detecting system 1, it may be configured such that the flow controller 11 is not disposed and the rectifier 12 is disposed. In addition, it may be configured such that the flow controller 11 is disposed and the rectifier 12 is not disposed.

In the above-described embodiments, the substrates 2 are formed in a rectangular flat plate shape. However, the present disclosure is not limited to the configuration. The outer shape of each substrate 2 may be a circular plate shape or a polygonal shape. The substrates 2 may include a protruding portion or a recessed portion on the outer shape.

The foregoing describes some example embodiments for explanatory purposes. Although the foregoing discussion has presented specific embodiments, persons skilled in the art will recognize that changes may be made in form and detail without departing from the broader spirit and scope of the invention. Accordingly, the specification and drawings are to be regarded in an illustrative rather than a restrictive sense. This detailed description, therefore, is not to be taken in a limiting sense, and the scope of the invention is defined only by the included claims, along with the full range of equivalents to which such claims are entitled.

This application claims the benefit of Japanese Patent Application No. 2021-188684, filed on Nov. 19, 2021, the entire disclosure of which is incorporated by reference herein.

INDUSTRIAL APPLICABILITY

The present disclosure is applicable to detection of a substance contained in gas.

REFERENCE SIGNS LIST

1 Substance detecting system
2 Substrate
2*a* Exposed portion
3 Through-hole
4 Substance sensor
5 Flow path
6 Vibrating beam
6A Drive beam
6B Detection beam
7 Sensitive film
8 Drive electrode
9 Detection electrode
10 Sensor
11 Flow controller
12 Rectifier
13A, 13B Housing
13*a* Inlet
13*b* Outlet
15 Internal frame
21 Drive signal line
22 Inter-electrode signal line
23 Detection signal line
31 Inflow hole
32 Branch path
32*a* Flow path
32*b* Both end portion
32*c* Flow path
33 Outflow hole
40 First rectification substrate
41 Second rectification substrate
G Gas
M1, M2, M3 Target substance

The invention claimed is:

1. A substance detecting system, comprising:

a plurality of substrates in each of which a plurality of through-holes through which gas flows is arranged and, in at least one of the through-holes, a substance sensor to detect a target substance contained in the gas flowing through the through-hole is installed, wherein by the substrates being stacked in such a manner that the through-holes communicate with each other, a plurality of flow paths for the gas, the flow paths extending in a stacking direction of the substrates, are formed, and in at least one of the flow paths, a plurality of the substance sensors are arranged.

2. The substance detecting system according to claim 1, wherein the substrates are stacked in such a manner that each of the flow paths is formed by the through-hole in which the substance sensor is installed and the through-hole in which the substance sensor is not installed alternately communicating with each other.

3. The substance detecting system according to claim 1, wherein a plurality of the substance sensors each of which detects one of different substances is arranged in the same flow path.

4. The substance detecting system according to claim 1, wherein each of the substance sensors includes:

a vibrating beam closing a portion of one of the through-holes;

a sensitive film film-formed on the vibrating beam in such a manner as to face an upstream side of a flow of the gas; and a signal outputter capable of outputting a signal indicating a change in a vibration state of the vibrating beam, the change being caused by adherence of the target substance contained in the gas passing through the through-hole on the sensitive film.

5. The substance detecting system according to claim 4, wherein regardless of sizes of cross sections of the through-holes orthogonal to a direction in which the gas flows, size of each of the vibrating beams is defined in such a manner that resonance frequencies of the vibrating beams are uniform among the through-holes.

6. The substance detecting systems according to claim 1, wherein a shape of each of cross sections orthogonal to a direction in which the gas flows in the through-holes is circular or polygonal.

7. The substance detecting system according to claim 6, wherein a boundary line between an edge of each of the through-holes and one of the vibrating beams is linear.

8. The substance detecting system according to claim 1, wherein sizes of cross sections of the through-holes orthogonal to a direction in which the gas flows are different from each other between substrates adjacent to each other.

9. The substance detecting system according to claim 8, wherein size of each of the cross sections of the through-holes in a substrate on a downstream side of the flow paths is larger than size of each of the cross sections of the through-holes in a substrate on an upstream side of the flow paths.

10. The substance detecting system according to claim 9, wherein size of a cross section of each of the flow paths orthogonal to a direction in which the gas flows increases in a continuous manner from an upstream side toward a downstream side of the flow path.

11. The substance detecting system according to claim 1, wherein the substrates are stacked in such a manner that positions of at least portions of outer sides of the substrates adjacent to each other are different from each other.

12. The substance detecting system according to claim 11, wherein shapes, directions, or sizes of outer shapes of the substrates adjacent to each other are different from each other.

13. The substance detecting system according to claim 12, wherein the substrates are stacked in descending order of size of an outer shape.

14. The substance detecting system according to claim 1, comprising:

a flow controller to draw in the gas from an outside and, while making flow of the gas constant, output the gas to the flow paths.

15. The substance detecting system according to claim 14, comprising:

a plurality of branch paths to divide the gas output from the flow controller into flows of gas having a same flow rate and flow velocity and send each of the flows of gas to one of the flow paths.

* * * * *